United States Patent [19]
Coupland

[11] Patent Number: 6,142,092
[45] Date of Patent: Nov. 7, 2000

[54] DEPTH CONTROL DEVICE

[75] Inventor: George M. Coupland, Norwich, United Kingdom

[73] Assignee: The Secretary of State for Defence in Her Britannic Majesty's Government of the United Kingdom of Great Britain and Northern Ireland, Hants, United Kingdom

[21] Appl. No.: 09/462,166

[22] PCT Filed: Jun. 25, 1998

[86] PCT No.: PCT/GB98/01858

§ 371 Date: Mar. 8, 2000

§ 102(e) Date: Mar. 8, 2000

[87] PCT Pub. No.: WO99/01338

PCT Pub. Date: Jan. 14, 1999

[30]   Foreign Application Priority Data

Jun. 13, 1997 [GB] United Kingdom .................. 9712415
Jul. 3, 1997 [GB] United Kingdom .................. 9713973

[51] Int. Cl.$^7$ .............................. B63G 8/14; B63B 22/20
[52] U.S. Cl. ............................................. 114/331; 441/29
[58] Field of Search ................................ 114/312, 331, 114/333; 405/171; 441/21, 28, 29, 133

[56]   References Cited

U.S. PATENT DOCUMENTS 3,436,776  4/1969  Davis .
4,031,581  6/1977  Baugh .
4,266,500  5/1981  Jurca .
5,303,552  4/1994  Webb ........................................ 60/496

FOREIGN PATENT DOCUMENTS 449 654   3/1913  France .
WO 93 17334  9/1993  WIPO .

*Primary Examiner*—S. Joseph Morano
*Assistant Examiner*—Patrick Craig Muldoon
*Attorney, Agent, or Firm*—Nixon & Vanderhye P.C.

[57]   ABSTRACT

A depth control device (1) for a subsmersible body comprises a depth monitor (5) and depth controller (6). A variable volume buoyant body operates under the control of the depth controller and comprises three chambers, the first (10) containing air and the second and third chambers (7, 8) containing hydraulic fluid. The second and third chambers (7, 8) communicate reversibly with one another by means of a tube (13) and bypass valve (12) in a pump (3), so that a piston (9) at the entrance to the first chamber (10) is displaced in response to movement of fluid between the second and third chambers. Thus, the volume of the buoyant body is varied and hence the buoyancy of the subsmersible body which it controls. To keep the submersible body at a particular depth, a depth trigger value is set in the depth controller (6), so that a reversible change in the volume of the buoyant body is initiated in response to a change in depth sensed by the depth monitor (5) by pumping fluid between the two chambers (7, 8). The depth monitor is generally a pressure sensor and the pump is typically a swash plate pump.

5 Claims, 1 Drawing Sheet

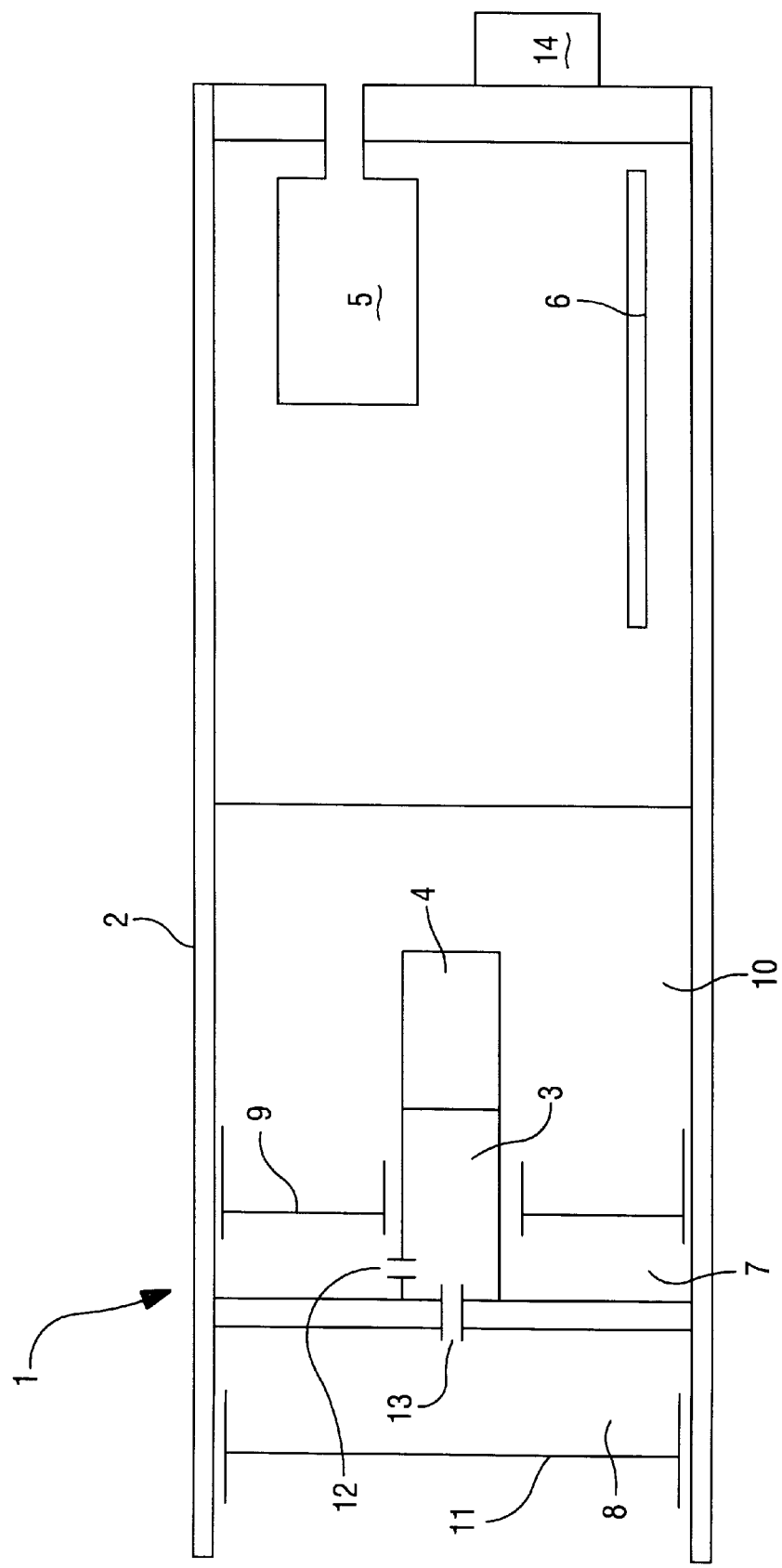

DEPTH CONTROL DEVICE

This invention relates to a depth control device, in particular for use with submersible bodies.

Certain submersible bodies, e.g. towed arrays, such as towed sonar arrays and seismic streamers, or sonar buoys, are required to maintain a predetermined depth. Other submersible bodies are deposited on the sea bed and must then be retrieved. Still others, such are autonomous underwater vehicles (AUV's) require an effective depth control mechanism as they move through the water. Conventionally, the towed arrays are towed behind a ship and are required to maintain neutral buoyancy at a particular depth. A sinker is applied to the end of the array nearest to the towing ship to position that end of the array correctly and the remainder of the array is made neutrally buoyant at the desired depth, either by adding and subtracting ballast from the array or pumping fluid, such as kerosene, into its housing until the correct level of buoyancy is reached. The disadvantage of these methods is that they are expensive in ship time and manpower and if the array is moved to an area where the salinity of the sea is different, the whole procedure must be repeated.

Another system which has been proposed is to attach moveable hydrofoils along the towed array and control the angle at which the hydrofoils are set, so that as the array is towed through the water its depth and stability can be maintained. U.S. Pat. No. 5,619,474 describes a system of this type. However, these hydrofoils create noise and can impair the performance of seismic sensors on a seismic streamer.

U.S. Pat. No. 3,909,774 suggests incorporating pressure sensors in sections of a seismic streamer towed by a ship to control inflow and outflow of a buoyancy control liquid held in a pipeline alongside the streamer and serving multiple sections. The problem with this system is that it is bulky and relies on a connection to a pump and supply on the ship for the additional fluid pipeline required, so it is unsuitable for small bodies or independent vessels, such as the AUV.

Retrieval of bodies, which do not have their own form of propulsion, from the sea bed is typically done by attaching an air bag and providing a tank of compressed air which inflates the air bag to give the body sufficient buoyancy to return to the surface. Another way is to ballast the body e.g. with lead shot, then to disengage the ballast, so that the natural buoyancy of the body raises it to the surface. Both of these methods are only suitable for single use and disposal of ballast is potentially damaging to the environment.

A device for deploying instrumentation has been proposed which is dependent on the external water pressure acting on a piston until the piston comes up against a spring and then the piston continues to compress the spring until, at a predetermined depth, a spike beneath the piston impales a gas canister. The gas released forces the piston back up and provides sufficient buoyancy to raise the device back to the surface of the water. The instrument is retrieved and the readings recorded during the device's passage can then be read. This system suffers from the similar problems to the ballast or air bag systems, that the devices must be set up for a specific depth in a particular area of water and can only be used for one depth setting without adjustment and replenishment of the gas canister. Use of this system in towed arrays would involve significant time and expense.

In accordance with a first aspect of the present invention, a depth control device for a submersible body, comprises depth monitoring means and depth control means; wherein the depth control means comprises a controller and a variable volume buoyant body; the buoyant body comprising a first chamber containing a first compressible fluid and second and third chambers in communicating relationship with one another containing a second fluid, less susceptible to compression than the first; whereby a piston at the entrance to the first chamber is displaced in response to movement of the second fluid between the second and third chambers such that the volume of the buoyant body is varied; and wherein a depth trigger value is set in the depth control means such that the controller initiates a reversible change in the volume of the buoyant body in response to a change in depth sensed by the depth monitoring means, whereby the depth of the submersible body is maintained at substantially the depth trigger value.

The present invention uses a buoyant body, the volume of which may be reversibly changed, to either increase or decrease the buoyancy of the body in response to a change in depth sensed by the depth monitoring means, and thereby maintain the depth at a set value. The invention uses a closed system which transfers the second fluid between two chambers, so that pressure is exerted indirectly on the more compressible first liquid allowing a self-contained, compact device to be produced.

A pump with an integral return valve is most suitable for the device of the invention and preferably, the pump comprises a swash plate pump.

The present invention uses a swash plate pump which increases or decreases the buoyancy of the device by transferring fluid between two reservoirs to alter the volume of fluid in a first chamber which provides the device with its buoyancy. There is no limit on how often this can be done, unlike systems which rely on compressed air, which have a limited usable life without refilling.

Preferably, the controller further comprises means to receive control signals to set the depth trigger value, such that the depth of the submersible body may be changed.

The invention can be operated to maintain a pre-set depth or to change the depth at which the body is held, by adjusting the buoyancy for a new depth trigger value.

Preferably, the depth monitoring means comprises a pressure sensor. Other ways of measuring depth include active acoustic means.

In accordance with a second aspect of the present invention a submersible body comprising one of a seismic streamer, a towed sonar array, a sonar buoy or a bathyscaph including at least one depth control device according to the first aspect.

Another way of deploying sonar is in a sonar buoy, instead of a towed array, which is usually tethered at a fixed depth and recovered by detaching itself from the tether. A depth control device of the invention would allow the buoy to be moved to different depths to obtain data.

An example of a depth control device according to the present invention will now be described with reference to the accompanying drawings in which:

The drawing illustrates a device according to the invention.

The drawing shows an example of a depth control device 1. The device 1 comprises a housing 2, a swash plate pump 3, a motor 4, a pressure transducer 5, electronic control circuits 6, first and second reservoirs 7, 8 and an air chamber 10. The first reservoir 7 is inside the housing 2 and a piston 9 is provided between the reservoir 7 and the air chamber 10. This piston 9 moves when hydraulic fluid, typically oil, is pumped between the first reservoir 7 and the second reservoir 8 by means of a tube 13 and bypass valve 12. The second reservoir is bounded by a second piston 11, separating the oil from water outside the housing, which moves to accommodate the distribution of the volume of oil between the two reservoirs 7, 8. The volume of the air chamber 10 varies to increase the buoyancy of the device 1 in response to a sensed increase in pressure or vice versa. The housing is preferably made of metal to be robust.

The control circuits 6 include a processor which may be programmed with a pressure corresponding to a desired depth at which the device 1 is to be maintained and when the pressure exceeds that programmed value, the buoyancy of the device 1 is increased by operation of the swash plate pump 3 to pump hydraulic fluid from the first reservoir 7 to the second reservoir 8, allowing the air to expand into the space vacated so increasing the volume of the air chamber 10 and the resultant buoyancy. If the pressure is below the programmed value, the buoyancy is reduced by reversing operation of the motor 4 and opening a bypass valve 12 which allows hydrostatic pressure on the piston 11 to push oil back from the second reservoir into the first reservoir, so compressing the piston 9 and reducing the volume of the air chamber 10. The fluid in the air chamber 10 is not restricted to air, other gases could be substituted.

The device may be connected to a body for which it is to control the depth via a watertight connector 13. The control circuitry may also include a receiver to receive control signals to change the programmed depth. The control signals could be delivered via internal cabling which is already in place in a towed array and connects directly to the ship or for a sonar buoy or other non-towed body, control signals may be transmitted from a remote transmitter on shore or on a ship or an aircraft. The active nature of the device of the present invention allows submersible bodies to be maintained at a predetermined depth or for the depth to be changed according to the circumstances. By making setting up pre-programmed consecutive variations to the programmed depth a body can operate at one or more depths for a period, surface and then move to a new depth. Alternatively, if a particular characteristic within a water column is of interest, additional sensors may be used to follow that characteristic and to control the programmed depth, so that a buoy passes through only the vertical section of the water column in which that characteristic is apparent.

The device can also be used to position and hold objects at a required depth e.g. for positioning equipment underwater by lowering the object under control to a pre-set depth and holding it at that depth whilst it is connected to other equipment. This reduces the cost of deployment as compared with an air bag system as currently used for this purpose which requires divers, cranage or ballasting.

What is claimed is:

1. A depth control device for a submersible body, the device comprising depth monitoring means and depth control means; wherein the depth control means comprises a controller and a variable volume buoyant body; the buoyant body comprising a first chamber containing a first compressible fluid and second and third chambers in communicating relationship with one another containing a second fluid, less susceptible to compression than the first; whereby a piston at the entrance to the first chamber is displaced in response to movement of the second fluid between the second and third chambers such that the volume of the buoyant body is varied; and wherein a depth trigger value is set in the depth control means such that the controller initiates a reversible change in the volume of the buoyant body in response to a change in depth sensed by the depth monitoring means, whereby the depth of the submersible body is maintained at substantially the depth trigger value.

2. A device according to claim 1, wherein the pump comprises a swash plate pump.

3. A device according to claim 1, wherein the controller further comprises means to receive control signals to set the depth trigger value, such that the depth of the submersible body may be changed.

4. A device according to claim 1, wherein the depth monitoring means comprises a pressure sensor.

5. A submersible body comprising one of a seismic streamer, a towed sonar array, a sonar buoy or a bathyscaph including at least one depth control device according to claim 1.

* * * * *

UNITED STATES PATENT AND TRADEMARK OFFICE
CERTIFICATE OF CORRECTION

PATENT NO. : 6,142,092
DATED : November 7, 2000
INVENTOR(S) : Mead et al.

It is certified that error appears in the above-identified patent and that said Letters Patent is hereby corrected as shown below:

Title page,
Item [75] Inventors should read:
Colin A. Mead, Dorset, United Kingdom; Alan T. Parsons, Dorset, United Kingdom; Stephen A. Pointer, Dorset, United Kingdom; Mark A. Bennett, Guildford, United Kingdom Signed and Sealed this Ninth Day of October, 2001

*Attest:*

NICHOLAS P. GODICI
*Acting Director of the United States Patent and Trademark Office*

*Attesting Officer*